United States Patent [19]

Banks et al.

[11] Patent Number: 4,490,478

[45] Date of Patent: Dec. 25, 1984

[54] OLEFIN DISPROPORTIONATION AND CATALYST THEREFOR

[75] Inventors: Robert L. Banks; Simon G. Kukes, both of Bartlesville, Okla.

[73] Assignee: Phillips Petroleum Company, Bartlesville, Okla.

[21] Appl. No.: 518,558

[22] Filed: Jul. 29, 1983

[51] Int. Cl.$^3$ .................... B01J 21/00; B01J 23/34; B01J 23/06; C07C 6/00

[52] U.S. Cl. .................... 502/254; 502/241; 502/253; 585/643; 585/646

[58] Field of Search .............. 502/241, 254, 253; 585/646, 643

[56] References Cited

U.S. PATENT DOCUMENTS

| | | | |
|---|---|---|---|
| 3,354,076 | 11/1967 | Beuther et al. | 502/254 |
| 3,513,109 | 5/1970 | Stiles | 502/254 |
| 3,792,106 | 2/1974 | Regier | 585/646 |
| 3,872,180 | 3/1975 | Nakatomi et al. | 585/646 |
| 3,939,096 | 2/1976 | Richardson | 502/241 |
| 4,221,768 | 9/1980 | Inoue et al. | 502/241 |

FOREIGN PATENT DOCUMENTS 2428820  9/1975  Fed. Rep. of Germany ...... 585/646

*Primary Examiner*—Delbert E. Gantz
*Assistant Examiner*—Chung K. Pak
*Attorney, Agent, or Firm*—Edward L. Bowman

[57] ABSTRACT

An improved olefin disproportionation catalyst produced by contacting an inorganic refractory oxide containing a catalytic amount of tungsten oxide or molybdenum oxide with a promoting amount of at least one elemental metal selected from zinc and manganese.

8 Claims, No Drawings

OLEFIN DISPROPORTIONATION AND CATALYST THEREFOR

BACKGROUND OF INVENTION

This invention relates to the disproportionation of olefins. In another aspect this invention relates to a disproportionation catalyst. In still another aspect, this invention relates to a novel method for producing a disproportionation reaction.

The disproportionation, or metathesis, of olefins is a reaction in which one or more olefinic compounds are transformed into other olefins of different molecular weights. The disproportionation of an olefin to produce one olefin of a higher molecular weight and one olefin of a lower molecular weight can also be referred to as self-disproportionation. For example, propene can be disproportionated to ethylene and cis- and trans-2-butene. Another type of disproportionation involves the codisproportionation of two different olefins to form still other olefins. An example would be the reaction of one molecule of 2-butene with one molecule of 3-hexene to produce two molecules of 2-pentene.

The term "disproportionation reaction" as used herein is intended to include all variations of disproportionation reactions including:

(1) The disproportionation of an acyclic mono- or polyene having at least three carbon atoms into other mono- or polyenes of both higher and lower number of carbon atoms; for example, the disproportionation of propylene yields ethylene and butenes; the disproportionation of 1,5-hexadiene yields ethylene and 1,5,9-decatriene;

(2) The conversion of an acyclic mono- or polyene having three or more carbon atoms and a different acyclic mono- or polyene having three or more carbon atoms to produce different acyclic olefins; for example, the conversion of propylene and isobutylene yields ethylene and isopentane;

(3) The conversion of ethylene and an internal acyclic mono- or polyene having four or more carbon atoms to produce other olefins having a lower number of carbon atoms than that of the acyclic mono- or polyenes; for example, the conversion of ethylene plus 4-methylpentene-2 yields 3-methylbutene-1 and propylene;

(4) The conversion of ethylene or an acyclic mono- or polyene having three or more carbon atoms with a cyclic mono- or cyclic polyene to produce an acyclic polyene having a higher number of carbon atoms than that of any of the starting materials; for example, the conversion of cyclohexene and 2-butene yields 2,8-decadiene; the conversion of 1,5-cyclooctadiene and ethylene yields 1,5,9,-decatriene;

(5) The conversion of one or more cyclic mono- or cyclic polyenes to produce a cyclic polyene having a higher number of carbon atoms than any of the starting materials; for example, the conversion of cyclooctene yields cyclohexadiene;

(6) The conversion of an acyclic polyene having at least 7 carbon atoms and having at least 5 carbon atoms between any two double bonds to produce acyclic and cyclic mono- and polyenes having a lower number of carbon atoms than that of the feed; for example, the conversion of 1,7-octadiene yields cyclohexene and ethylene; or (7) The conversion of one or more acyclic polyenes having at least three carbon atoms between any two double bonds to produce acyclic and cyclic mono- and polyenes generally having both a higher and lower number of carbon atoms than that of the feed material; for example, the conversion of 1,4-Pentadiene yields 1,4-cyclohexadiene and ethylene.

SUMMARY OF THE INVENTION

In accordance with the present invention, a disproportionation catalyst comprising inorganic refractory oxide containing a catalytic amount of a metal oxide selected from the group consisting of tungsten oxide and molybdenum oxide is improved by contacting said catalyst with a promoting amount of at least one elemental metal selected from the group consisting of zinc and manganese under conditions suitable for said metal to promote the activity of said metal oxide.

DESCRIPTION OF PREFERRED EMBODIMENTS

The inorganic refractory oxide comprises solid inorganic oxide support. The term inorganic refractory oxide is used herein to include those inorganic solid supports containing metal and oxygen atoms which are stable during the temperature conditions used in the disproportionation reaction. Such materials include, for example, silica, alumina, magnesia-alumina, silica-alumina, titania-alumina, zirconia-alumina, alumina-titania-zirconia and phosphates of thorium, aluminum, zirconium, titanium, calcium, and magnesium. Preferred refractory metal oxides are alumina or silica refractory oxides, especially high purity forms such as those containing at least 99 percent of alumina or silica. Generally, the refractory oxide has a surface area of at least 25 m$^2$/g and preferably the surface area is from 100 m$^2$/g.

The metal oxides, i.e. tungsten oxide and molybdenum oxide, can be combined with the refractory oxide support in any conventional manner such as dry mixing, impregnation from a diluent, ion exchange, or the like. The oxides can be added directly or in the form of metal compounds that can be converted to oxides by calcination. The calcination is conducted by heating the impregnated refractory oxide in the presence of a nonreducing gas, such as nitrogen, argon, carbon monoxide, or oxygen-containing gas such as air, under conditions sufficient to convert the metal compound to the oxide. Temperatures in the range of about 350° C. to about 800° C. are generally satisfactory for such calcination.

The proportion of the metal oxide combined with the refractory oxide can be varied, but generally the refractory oxide will contain at least 0.1 percent by weight of metal oxide, with amounts from about 0.2 to 50 percent by weight being preferred, and 1 to 15 percent especially preferred, said weight percent being based upon the combined weights of the refractory oxide and the metal oxide.

The tungsten oxide or molybdenum oxide catalyst in then combined with a promoting amount of a metal selected from zinc and manganese. The amount of promoting metal can vary widely depending upon the level of activation and catalyst life desired. Generally the elemental metal will be employed in an amount in the range of 0.5 to 50, preferably 2 to 30 weight percent based on the weight of the supported metal oxide catalyst prior to the addition of the elemental metal.

The elemental metal can be combined with the catalyst in any suitable manner. The metal in a powdered form can be admixed with the catalyst or more preferably the metal is applied to the catalyst in a molten or vaporous form. This can be accomplished, for instance, by melting the metal and dropping the molten metal on the catalyst or by passing a stream of inert gas such as nitrogen or argon through the molten metal and then over the catalyst.

It is essential that the combination of the elemental metal and the catalyst be heated to an elevated temperature sufficient to cause the promotion to take place. Generally, this involves heating the catalyst to at least the melting temperature of the elemental metal. The length of time heating the catlayst composite is generally in the range of about 1 minute to about 10 hours, preferably on the order of about 10 minutes to about 30 minutes. It is accordingly currently preferred to apply the metal to a bed of the catalyst and then flow a suitable gas, such as nitrogen, through the bed at the melting temperature of the metal for a length of time sufficient to obtain a substantial distribution of the metal in the catalyst. The resulting catalyst is then immediately suitable for use in the disproportionation reaction. Generally the temperature and time required can be determined by observing the catalyst while it is being heated. Generally, there will be an obvious color change in the catalyst which can be used as an indicator that the catalyst is ready for use.

An oxidizing atmosphere has been found to have an adverse effect upon the promoting effect of the elemental metals. Accordingly, it is desirable to protect the promoted catalyst from oxidizing atmosphere particularly while the catalyst is at temperatures greater than about normal room temperature. This can be done by keeping the promoted catalyst under a nondeleterious atmosphere, such as nitrogen, until use.

The promoted catalyst can be used in disproportionation reactions in a conventional manner. The reaction temperature can vary depending upon the type of refractory oxide employed. Typically, the disproportionation is carried out at a temperature in the range of about 100° to about 600° C., preferably about 200° to about 500° C. Generally, a temperature in the range of about 100° to 300° C. is preferred when an alumina support is employed and about 200° to 500° C. when a silica support is employed.

The disproportionation reaction can be carried out by contacting the olefins to be disproportionated with the catalyst in the liquid phase or the gas phase, depending on structure and molecular weight of the olefins, temperature and pressure.

The pressure during the disproportionation reaction may vary between wide limits. Pressures between 0.1 and 500 atm. are suitable; preferred pressures are between 1 and 40 atm.

If the reaction is carried out in the liquid phase, solvents or diluents for the reactants may be ued. Aliphatic saturated hydrocarbons (e.g. pentane, hexane, cyclohexane, dodecane) and aromatic hydrocarbons such as benzene and toluene are suitable. If the reaction is carried out in the gaseous phase, diluents such as aliphatic hydrocarbons (e.g. methane, ethane, and/or substantially inert gases (e.g., nitrogen, carbon dioxide) may be present. Preferably the disproportionation reaction is effected in the absence of dry significant amounts of deactivating materials such as water and oxygen.

The length of time during which the olefinically unsaturated compounds to be disproportionated are contacted with the catalyst is not very critical, and may conveniently vary between 0.1 seconds and 24 hours, although longer and shorter contact times may be used. The contact time needed to obtain a reasonable yield of disproportionated products depends on several factors such as the activity of the catalyst, temperature, pressure and structure of the olefinically unsaturated compounds to be disproportionated.

The process of the invention can be effected batchwise or continuously, with fixed catalyst beds, slurried catalysts, fluidized beds or by using any other conventional contacting techniques. The solid disproportionation catalysts are applied in any appropriate form, for example, as powders, flakes, pellets, spheres or extrudates.

The olefinic products, for the most part, have established utility as precursors of polymers, e.g., as the third component of ethylene-propylene terpolymers useful as synthetic elastomers. Cleavage of the ethylenic bonds of polyolefinic products as by ozonization produces di- or polycarboxylic acids which are reacted with diamines, e.g., hexamethylenediamine, to form Nylons which are useful in synthetic fibers. The olefinic products are converted to secondary and tertiary alcohols as by sulfuric acid-catalyzed hydration. Alternatively, the olefinic products are converted by conventional "Oxo" processes to aldehydes which are hydrogenated with conventional catalysts to the corresponding alcohols. The $C_{12}$–$C_{20}$ alcohols thereby produced are ethoxylated as by reaction with ethylene oxide in the presence of a basic catalyst, e.g., sodium hydroxide, to form conventional detergents and the lower molecular weight alcohols are esterified by reaction with polybasic acids, e.g., phthalic acid, to form plasticizers for polyvinyl chloride.

A further understanding of the present invention and its advantages will be provided by reference to the following examples.

EXAMPLE I

A $WO_3.SiO_2$ catalyst containing about 6 weight percent $WO_3$ was prepared by adding an aqueous solution of ammonium metatungstate to Davidson Grade 59 silica gel, 20–40 mesh particles, then evaporating to dryness, and then calcining in dry air at about 500° C.

The effectiveness of the catalyst in disproportionation was determined by placing a bed of the catalyst in a tubular reactor and heating in air for about 30 minutes at about 625° C. to provide activation. The catalyst was maintained at about 625° C. for about 30 minutes under flowing nitrogen and then cooled to about 400° C. Substantially pure propylene dried by being passed through alumina and magnesium oxide was then passed through the reactor at a temperature of around 400° C. The percent conversion of propylene after use for one hour was 13.5.

EXAMPLE II

Another portion of the $WO_3.SiO_2$ catalyst of Example I was placed in a tubular reactor. As before the catalyst was heated at 625° C. for 30 minutes in the presence of air. Then it was flushed with nitrogen for 5 minutes at 625° C. Still under flowing nitrogen the catalyst was cooled to room temperature and then zinc metal was placed on top of the bed in an amount equal to 10 weight percent of the catalyst bed. The bed was then heated back up to 625° C. and held at that temperature for 45 minutes under nitrogen. By this time most of the catalyst bed had turned dark blue. The bed was then cooled down to 400° C. and the substantially pure propylene flow begun. The percent conversion at 400° C. after about one hour was 48.9, more than 3 times that of the unmodified catalyst of Example I.

In other runs with more and less than 10 weight percent zinc employed, the zinc modified catalysts provided better conversion than the control catalyst of Example I.

EXAMPLE III

A run was made to determine how the effect of elemental zinc compared to that of zinc oxide. About 5 grams of the catalyst of Example I was impregnated with an aqueous solution of zinc nitrate. The amount of zinc nitrate was such that when converted to the oxide it would be equivalent to 2.84 grams of ZnO. After the aqueous solution was poured on the catalyst the liquid was evaporated by heating on a hot plate and then placed in an oven overnight for further drying.

The resulting catalyst was activated in the tubular reactor, as before, by heating in the presence of air at 625° C. for 45 minutes. Then the catalyst bed was flushed with $N_2$ at 625° C. for 45 minutes. The temperature was lowered to 400° C. and the propylene flow begun. The propylene conversion after 1 hour at 400° C. was no more than 1 percent. This demonstrates that the effect of elemental zinc is quite different than that of zinc oxide.

EXAMPLE IV

Another portion of the $WO_3.SiO_2$ catalyst of Example I was placed in the tubular reactor. The catalyst was heated at 625° C. for 30 minutes under air. Then it was flushed with nitrogen while being cooled. When the temperature was below 200° C. enough manganese was added in an amount equal to about 15 weight percent of the catalyst bed, 0.22 g of Mn on 1.5 g of $WO_3.SiO_2$. Nitrogen was then flowed through the bed for 30 minutes at a temperature of 625° C. The bed was then cooled to 400° C. and the substantially pure propylene flow begun. The percent conversion at 400° C. after about one hour was 22.3 percent, almost twice that of Example I.

In other runs with more and less manganese, the modified catalysts still provided better conversion than the control catalyst of Example I.

EXAMPLE V

A run was made to determine how the effect of elemental manganese compared to that of manganese oxide. The prepare the catalyst 1.5 grams of the 6 wt. % $WO_3.SiO_2$ was admixed with 0.4 grams of 4–12 mesh manganese dioxide.

The resulting mixture was placed in the tubular reactor and activated by heating at 650° C. for 20 minutes then purging with nitrogen at 650° C. for about an hour. The temperature was then lowered to 400° C. and the propylene flow began. The propylene conversion after 1 hour at 400° C. was less than 2 percent. This demonstrates that the effect of elemental manganese is quite different from that of manganese dioxide.

What is claimed is:

1. A composition useful as a catalyst for the disproportionation of olefins comprising the product obtained by contacting a refractory oxide containing a metal oxide selected from the group consisting of tungsten oxide and molybdenum oxide with a promoting amount of at least one elemental metal selected from the group consisting of zinc and manganese under conditions suitable for said metal to promote the activity of said metal oxide for the disproportionation reaction.

2. A composition according to claim 1 wherein said inorganic refractory oxide is selected from the group consisting of silica, alumina, and mixtures thereof.

3. A composition according to claim 2 wherein said metal oxide consists essentially of tungsten oxide and the amount of tungsten oxide is equal to about 1 to about 15 weight percent of the combined weights of said tungsten oxide and said refractory oxide.

4. A composition according to claim 3 where said refractory oxide comprises silica.

5. A composition according to claim 4 wherein said elemental metal is employed in an amount in the range of about 0.5 to about 20 weight percent of the combined weights of the tungsten oxide and the silica prior to the addition of said metal.

6. A composition according to claim 5 wherein said metal consists essentially of zinc.

7. A composition according to claim 5 wherein the amount of zinc is in the range of 2 to 30 weight percent based on the weight of the supported metal oxide catalyst prior to the addition of the elemental zinc.

8. A composition according to claim 5 wherein said metal consists essentially of mangangese.

* * * * *

UNITED STATES PATENT AND TRADEMARK OFFICE
CERTIFICATE OF CORRECTION

PATENT NO. : 4,490,478

DATED : December 25, 1984

INVENTOR(S) : Robert L. Banks et al

It is certified that error appears in the above-identified patent and that said Letters Patent is hereby corrected as shown below:

Column 6, line 43 (claim 7), "5" should read --- 6 ---.

Signed and Sealed this

Twenty-first Day of May 1985

[SEAL]

Attest:

DONALD J. QUIGG

Attesting Officer

Acting Commissioner of Patents and Trademarks